United States Patent [19]
Hammond et al.

[11] Patent Number: 6,014,212
[45] Date of Patent: Jan. 11, 2000

[54] METHOD AND APPARATUS FOR SPECTROPHOTOMETRICALLY ANALYSING CHARACTERISTICS OF A TABLET

[75] Inventors: Stephen Victor Hammond; Tony Graham Axon; Rachel Brown, all of Sandwich, United Kingdom

[73] Assignee: Pfizer Inc., New York, N.Y.

[21] Appl. No.: 09/129,115

[22] Filed: Aug. 4, 1998

[30] Foreign Application Priority Data

Aug. 8, 1997 [GB] United Kingdom .................... 9716911

[51] Int. Cl.$^7$ .................................................. G01N 21/01
[52] U.S. Cl. .................... 356/319; 356/244; 250/339.07; 250/339.12
[58] Field of Search .................................. 356/300, 319, 356/326, 328, 244; 250/339.07, 339.12, 339.01

[56] References Cited

U.S. PATENT DOCUMENTS

| 4,882,493 | 11/1989 | Lodder et al. | 250/353 |
| 5,214,277 | 5/1993 | Drennen, III | 250/216 |
| 5,750,966 | 5/1998 | Drennen, III et al. | 250/341.2 |

FOREIGN PATENT DOCUMENTS 0436338  12/1990  European Pat. Off. .

*Primary Examiner*—F. L. Evans
*Attorney, Agent, or Firm*—Peter C. Richardson; Gregg C. Benson; Robert T. Ronau

[57] ABSTRACT

A method of and apparatus for spectrophotometrically analyzing a tablet by NIR transmission measurements includes a tablet holder 1 having a recess 5 within which a tablet 20 is located. A probe 40 is applied to the tablet 20 to direct an NIR beam 45 to and through the tablet for sensing at a detector 32 from which measurements characteristics of the tablet are analyzed. The recess 5 accommodates the tablet 20 as a close, possibly complementary fit. The tablet is clamped in the recess 5 by a spring loaded rod 8 to ensure that the tablet is located and retained at a predetermined position in the recess 5 relative to an aperture 7 through which the transmitted beam is directed to the detector 32. Preferably the tablet 20 is subjected to clamping forces applied by two spring loaded clamping rods disposed substantially perpendicularly relative to each other in the tablet holder. The effect of clamping the tablet in the tablet holder permits reproducible analysis measurements to be achieved from which may be determined the acceptability or otherwise of the characteristics of tablets as manufactured commercially. The invention also provides for the structure of a tablet holder.

29 Claims, 5 Drawing Sheets

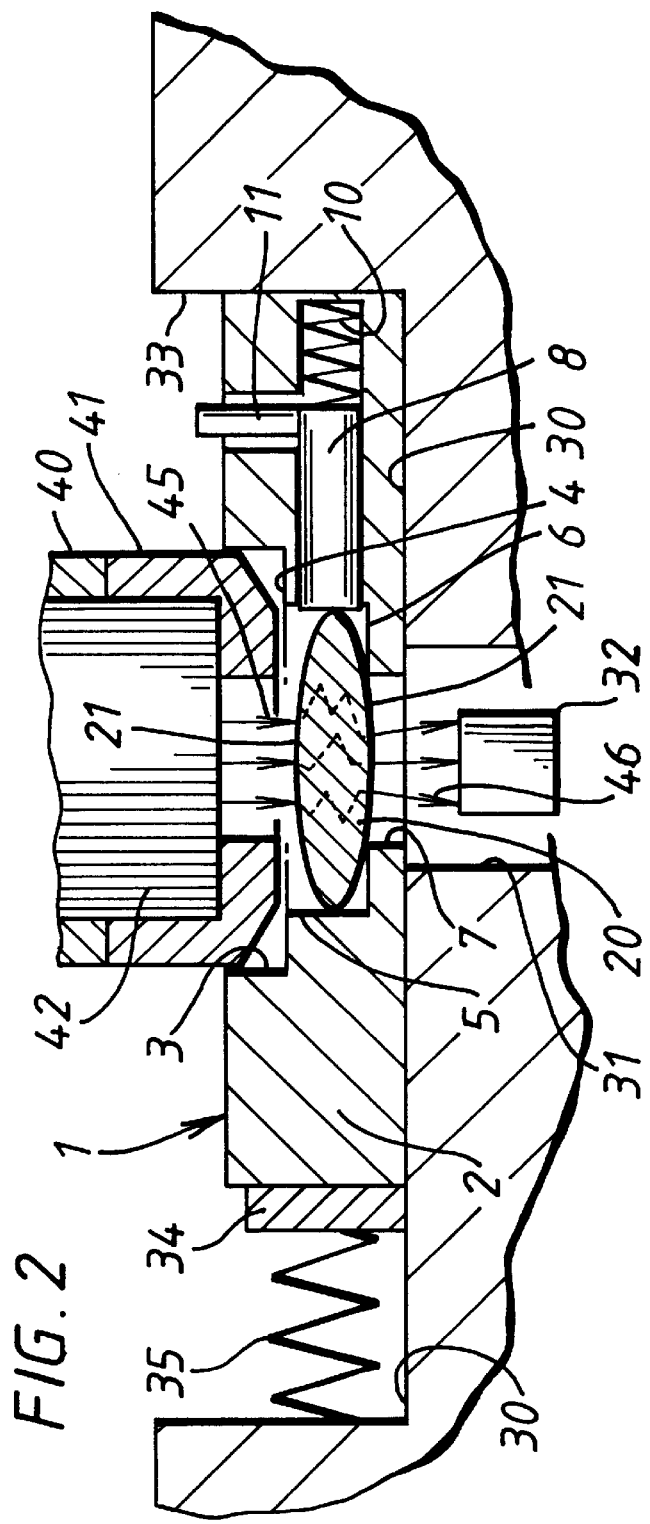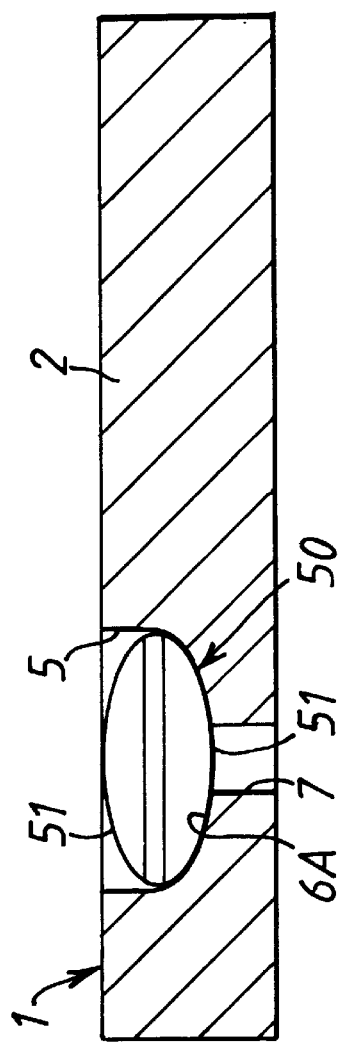

METHOD AND APPARATUS FOR SPECTROPHOTOMETRICALLY ANALYSING CHARACTERISTICS OF A TABLET

TECHNICAL FIELD & BACKGROUND ART

The present invention relates to spectrophometric analysis and is particularly concerned with a method of, and apparatus for, such analysis of a tablet (primarily material of the tablet) by measurements of a beam of electromagnetic radiation (usually near infrared) transmitted through the tablet.

Spectrophotometric analysis is a well known facility for providing quantitative and qualitative measurements or assessments of organic and biological substances and materials, especially pharmaceutical materials. In the pharmaceutical industry it is necessary to analyse tablets randomly selected from a production batch to ensure that the characteristics of the tablets fall within tolerances of a particular specification; this particularly concerns the identity of the constituents, content uniformity, potency, hardness and thickness of the tablets. The identity, content uniformity and potency of tablet material are of especial importance and a well known and popular technique for assessing these characteristics is by spectrophotometric analysis of reflectance measurements which result from a beam of near infrared (NIR) radiation applied to the material of the tablet. Typical near infrared spectrophotometers suitable for providing reference spectra are sold under the Trade Marks COMPSCAN by The Gardner Neotech Division of Pacific Scientific and MODEL 6500 (together with a Rapid Content analyser) by Foss Electric. It is recognised however that analysis of a tablet per se by near infrared (NIR) reflectance measurements has the disadvantage that it is not possible to clearly distinguish between different tablet types or tablets with varying potency (drug content) or hardness. This is because only the surface of the tablet is scanned.

Therefore only a small part of the tablet sample is analysed and this may not be representative of the whole tablet. For example, reflectance measurements from a typical pharmaceutical tablet will result from near surface regions of the tablet (which are likely to correspond with a penetration depth for the NIR beam in the order of 0.5 millimeters) and clearly this will not provide a reliable indication of the overall structure or characteristics of a tablet whose thickness is considerably in excess of 0.5 millimeters. It has not been possible therefore to rely on NIR reflectance measurements of pharmaceutical tablets to assess whether or not a production batch of those tablets is acceptable for marketing. Because of these problems it is conventional practice to analyse the material of a tablet by destructive testing. This may include reducing the tablet to powder and subjecting it to analysis, including that by NIR reflectance measurements. Such analysis has been found to provide a greater order of accuracy and reliability when effected on a material in powder form as compared with that derived from the material when in tablet form.

Because of the necessity to ensure that the characteristics of the material of a pharmaceutical tablet meet a predetermined specification, the procedure for analysing tablets at frequent intervals during or following production of a batch of tablets adds considerably to the production cycle time, that is the time it takes to manufacture a tablet from its basic ingredients to when the tablet is packaged ready for marketing. It is not unusual, and indeed may be typical, for an actual manufacturing cycle time of a pharmaceutical tablet to be in the order of five to seven times longer than a theoretically determined manufacturing cycle time. Bearing in mind that it is not unusual for the theoretical manufacturing cycle time to be from five to twenty five days, it will be appreciated that the differential between the theoretical and actual cycle times adds considerably to the manufacturing costs, principally in the costs of administering and storing the pharmaceutical product. An appreciable part of the administration costs results from delays in analysing the characteristics of a tablet to ensure that it attains a predetermined specification and as a consequence a batch of tablets manufactured and ready for marketing may be held up for several days awaiting acceptable analysis reports before they can actually be released to the market.

In an attempt to overcome the disadvantages of the above described tablet analysis techniques it has been proposed to provide a rapid non-destructive quality assessment of tablets using spectrophotometric analysis of a tablet by transmission measurements resulting from a beam of electromagnetic radiation (usually near infrared) passing through the tablet. By this technique the full thickness of the tablet is analysed giving a spectrum which is representative of the whole tablet and this should make it possible to achieve a quick release of tablets during production with the aim of reducing the actual manufacturing cycle time. An example of a spectrophotometer utilising near infrared transmission through a tablet is an analyser sold under the Trade Mark INTACT by Foss Electric. This tablet analyser has a tablet holder in the form of a plate-like body in which a recess is provided, such recess being intended to accommodate a tablet for analysis. In a bottom face of the recess is located an aperture through which NIR radiation transmitted through the tablet is directed to a detector of the spectrophotometer. The detector is responsive to the transmitted radiation and provides measurements for analysing characteristics of a tablet that is located in the recess. The tablet is a close fit in the recess to overlie the aperture whilst the tip of a fibre optic probe (through which the NIR beam is provided) is moved onto the tablet to direct the NIR beam through it. A typical pharmaceutical tablet will have a relatively dense structure and good reflectance characteristics and research has indicated that only (approximately) 0.5% of the intensity of the NIR beam that is applied to the tablet will be transmitted through the tablet to the detectors. As a consequence a through tablet analyser has to be extremely sensitive to respond to the NIR radiation to which its detectors are subjected for analysis purposes; because of this sensitivity our research has indicated that with known methods and apparatus the repeated analysis of a tablet is inconsistent or not reproducible. As a result the analysis of a particular pharmaceutical tablet could not be relied upon to determine whether or not the characteristics required of that tablet had been met to permit a batch of the tablets to be released to the market or for manufacture of the tablets in that batch to continue. By way of example, FIG. A of the accompanying illustrative drawings shows the spectra acquired of a typical pharmaceutical tablet in the tablet analyser as aforementioned in which the ordinate shows a level of absorbence and the abscissa the wavelength. The several graphs were determined from repeated analysis of the same tablet which was removed from the analyser and replaced to be scanned and subjected to analysis on ten successive occasions. For each of the ten scannings the orientation of the tablet in the recess was maintained constant. This was considered to be important as it is usual for tablets to be embossed or otherwise marked on one side face with a trade name or other identification and on the other side face with a score line (along which the tablet may easily be broken) so that changing the orientation of the tablet to present a different side face to the source of NIR radiation could unreasonably have altered the conditions under which the analysis was effected. It will be seen that the graphs indicate a wide variation in the absorbence levels that were determined for a particular wavelength. Accordingly if it is known that a particular pharmaceutical compound to be acceptable in the tablet has to provide absorbence within a predetermined range for a given wavelength and this range of absorbence is less than that exhibited by the extremes of the graphs derived from the analysis results, it would be inappropriate to rely on the analysis in deciding whether or not the constitution of the tablet is acceptable. There is therefore a need for both a method of, and an apparatus for, spectrophotometric analysis of the characteristics of a tablet from measurements of a beam of electromagnetic radiation transmitted through the tablet whereby the analysis is sufficiently accurate and reproducible so that it can be relied upon for determining the acceptability or otherwise of tablets as manufactured and thereby provide a rapid and non-destructive quality assessment to enable the quick release of tablets during production with the aim of reducing the manufacturing cycle time. It is an object of the present invention to provide a method and apparatus for spectrophotometric analysis which lends itself towards satisfying the aforementioned need.

STATEMENTS OF INVENTION & ADVANTAGES

According to the present invention there is provided a method of spectrophotometrically analysing characteristics of a tablet by transmission measurements from a beam of electromagnetic radiation applied to and passing through the tablet which comprises locating the tablet in a recess to overlie an aperture through which aperture radiation from the beam transmitted through the tablet is applied to a detector for analysis measurements, characterised by applying to the tablet a clamping force in a direction substantially perpendicular relative to the direction in which the beam is applied to the tablet and which clamping force serves to secure the tablet at a predetermined position within and relative to the recess.

Further according to the present invention there is provided spectrophotometric apparatus for analysis of characteristics of a tablet by transmission measurements from a beam of electromagnetic radiation applied to and passing through the tablet which comprises a recess for accommodating a tablet during the analysis, said recess having a bottom face in which is located an aperture through which radiation transmitted through the tablet is directed, and a detector responsive to said transmitted radiation for analysing characteristics of the tablet, and in which clamping means is provided for securing a tablet in the recess by applying a clamping force to the tablet in a direction substantially perpendicular relative to the direction in which the beam is applied to the tablet to displace the tablet relative to the recess to a predetermined position in the recess and to secure the tablet at said predetermined position in the recess.

Still further according to the present invention there is provided a spectrophotometric analysis tablet holder comprising a body, a recess in the body for accommodating a tablet, said recess having a bottom face in which is located an aperture through which radiation transmitted through the tablet is to be applied to a detector for analysing characteristics of the tablet and in which clamping means is carried by the body for securing a tablet in the recess by applying a clamping force to the tablet to displace the tablet relative to the recess to a predetermined position in the recess and to secure the tablet at said predetermined position in the recess.

With known tablet spectrophotometric analysers utilising transmission measurements it is usual for the recess to be formed so that its periphery corresponds to the periphery of the tablet which is to be subjected to analysis and for the tablet to be received as a close substantially complementary fit within the recess. Such a fit between the recess and tablet serves to locate the tablet over the aperture and also to alleviate stray NIR radiation from reflecting around the tablet (between the tablet and the recess) to enter the aperture other than by transmission through the tablet. However whilst the tablet may be a close fit between its periphery and a complementary peripheral wall of the recess, some clearance will necessarily be provided between the tablet and the recess to facilitate tablet interchange. Bearing in mind the sensitivity of the apparatus as previously discussed for NIR transmission systems, our research has indicated that this clearance, small though it is, is nevertheless sufficient to permit small variations in the positioning of the tablet within the recess and these small variations (which may, for example, be caused by vibrations or by general positioning of the tablet in the recess) are sufficient to cause the unacceptable variations in the reproducibility of the analysis spectra as discussed above with reference to FIG. A. By applying a clamping force to the tablet in accordance with the present invention so that the tablet will be secured within the recess at a constant position (to which it is displaced and secured by the clamping force), the tolerance or clearance provided between the periphery of the tablet and the peripheral wall of the recess is effectively taken up. It can thus be ensured that the tablet (or successive similar tablets which are subjected to analysis) will be biased and located at substantially the same position relative to the aperture to provide substantially reproducible analysis results.

As aforementioned, it will be usual for tablets to be provided with embossing and/or score lines so when similar tablets from a batch of tablets are subjected to analysis it is important to ensure that the tablets are similarly orientated within the recess. Usually the area of the aperture within the recess will be relatively small in comparison with the face of the tablet which overlies the aperture so that if the area of the tablet which overlies the aperture includes a score line or embossing, the profile presented by such embossing or score line can have a considerable effect upon the radiation which is transmitted through the tablet for analysis purposes. With this in mind a small displacement of the tablet (with consequential small displacement of the embossing or score line) relative to the recess (as may be caused by fitting the tablet to the recess or by vibration as the tablet holder is fitted to the spectrophotometric apparatus) can result in the unacceptable inconsistent analysis measurements previously discussed; the clamping force applied to the tablet in accordance with the present invention will again alleviate this problem by ensuring that the tablet is secured relative to the recess with the embossing or score line at a constant position relative to direction in which the beam is applied to the tablet. The aforementioned "predetermined position" can thus be considered as that position in the recess to which each tablet of a batch of identical tablets will be displaced by the clamping force irrespective of the initial positioning of the tablets in the recess and which predetermined position will be the same for all of the tablets in the batch when the tablets are similarly orientated in the recess. Conveniently the clamping force is applied by one or more spring loaded members such as plates carried by the body of a tablet holder. The spring loaded member may be provided with a lever for convenience of manually displacing the member against its biasing to facilitate location and removal of the tablet from the recess. The spring loaded member or other clamping means may be profiled to co-operate in substantially complementary manner with the part of the tablet surface with which it engages.

As previously mentioned, it is preferred that the recess has a peripheral shape which is substantially complementary to the peripheral shape of the tablet so that the tablet is received as a close fit within the recess. Consequently the recess will usually be formed for a particular shape and size of tablet which is intended to be manufactured commercially. Typical tablets will have a round, polygonal (usually hexagonal or rectangular), trapezoidal, triangular, oval or star peripheral shape.

Because of the sensitivity of spectrophotometers used to provide spectra derived by transmission through tablets it is desirable that the tablet when fitted to the recess seals the aperture to the extent that all of the electromagnetic radiation which passes through the aperture for analysis purposes is derived by transmission through the tablet. However, it is realised that in practice it will be extremely unlikely for a tablet to be fitted to the recess to form a perfect seal with the periphery of the aperture, particularly when the tablet has been subjected to its clamping force. Nevertheless, it is desirable that the recess is in the form of a seating for the tablet, which seating accommodates the tablet to alleviate the passage of NIR or other radiation over the surface of the tablet between the tablet and the recess (i.e. stray radiation) to enter the aperture otherwise than by transmission through the tablet. This is particularly so when the face of the tablet which opposes a bottom face of the recess is embossed or scored. Preferably therefore the recess is formed with a bottom face which presents a substantially complementary profile to a face of the tablet which is received in the recess for that face of the tablet to co-operate with the bottom face of the recess in substantially complementary fashion. Thus where the tablet has a flat face, the bottom of the recess may be flat for the two faces to abut in substantially face-to-face manner and minimise stray light which enters the aperture otherwise than by transmission through the tablet. Similarly where the tablet has a part spherical or a part cylindrical face, the recess may be formed with a concave profile of substantially complementary shape. It will be appreciated however that such complementary relationship between the bottom face of the recess and an opposing face of the tablet is not essential; for example, where the tablet has a part spherical face the recess may have a flat bottom face with a circular aperture therein so that the part spherical face of the tablet sits in the aperture to form a light or radiation seal about the periphery of the aperture. Whilst an efficient radiation seal is preferred to minimise stray radiation being applied through the aperture to the detector other than by transmission through the tablet, it will be appreciated that such stray radiation as may be applied to the detectors will substantially be the same for all of the tablets in a batch because each of the tablets when similarly orientated in the recess will be displaced to and secured in substantially the same position by the clamping force to which it is subjected.

In addition to subjecting the tablet to a clamping force by clamping means carried by the tablet holder so that the tablet is biased to a predetermined position in a direction perpendicular relative to the direction in which the radiation beam is applied to the tablet, the tablet may be subjected to pressure applied in the direction of the radiation beam to bias the tablet against the bottom face of the recess. Such pressure on the tablet is conveniently effected by abutting the tablet with the tip of a probe from which the electromagnetic radiation emanates (contact between the probe and tablet being desirable to alleviate stray radiation passing over the periphery of the tablet to enter the aperture other than by transmission through the table).

As previously implied, it is preferred that the recess within which the tablet is accommodated is provided in a tablet holder which is readily removable from and inserted into the spectrophotometer for convenience of changing tablets. Such a tablet holder, which will usually be in the form of a metal plate, when fitted to the apparatus preferably locates its aperture and therefore the recess at a predetermined and constant position relative to the detector to ensure that there are no variations in positioning between the aperture/recess and the detector (which variations could adversely affect the reproducibility of analysis measurement. Usually the tablet holder plate will be spring biased or otherwise secured to be urged automatically into and maintained at its predetermined position within the apparatus.

Following from the method and apparatus of the present invention, we have determined that it is possible to provide spectra derived from transmission through tablets which are consistent and readily reproducible and from which characteristics of the tablet may be measured and derived with sufficient accuracy to determine whether the tablet has been manufactured in accordance with a predetermined specification. The invention thus provides the considerable advantage, for example, that manufacture of a particular batch of tablets (from which the tablet analysed was randomly selected) may continue or that the batch may be directed immediately following manufacture to packaging without the customary delay in effecting quality assessment as has hitherto been the case. This quality assessment by use of the method and apparatus of the invention has been found acceptable for the identification of tablets of various products, including the ability to distinguish between different dose weights of the same products; to distinguish between tablets with varying hardness and provide a quantitative measurement for hardness; to determine the content uniformity of tablets in a batch; to distinguish between individual tablets of varying potency and to provide reliable quantitative assay for the tablets and to produce a qualitative test by which tablets can be checked for correct thickness during production. By way of comparison, FIG. B of the accompanying illustrative drawings shows a graph with a similar ordinate and abscissa to that of FIG. A and which is derived from the same tablet as that which was subjected to analysis for the measurements shown in FIG. A. The graph shown in FIG. B results from the tablet being subjected to ten scannings in an identical manner to the ten scannings which are utilised for the FIG. A graphs but in FIG. B the scannings were carried out in accordance with the method and with the apparatus of the present invention. It will immediately be apparent that the graphs of all of the scannings in FIG. B coincide to provide a single line graph from which characteristics of the tablet may be determined with an accuracy acceptable for pharmaceutical manufacturing purposes.

DRAWINGS

One embodiment of a method and apparatus for the spectrophotometric analysis of characteristics of a tablet by measurements of NIR transmission through the tablet will now be described, by way of example only, with reference to the accompanying illustrative drawings, in which:

FIG. 1 is a plan view of a tablet holder constructed in accordance with the present invention;

FIG. 2 diagrammatically illustrates a side elevation, in part section, of spectrophotometric apparatus constructed in accordance with the present invention and which includes the tablet holder of FIG. 1, the tablet holder being shown in section on the line II—II of FIG. 1;

FIG. 4 is a section of the tablet holder in FIG. 3 taken on the line IV—IV;

Figure 5A:
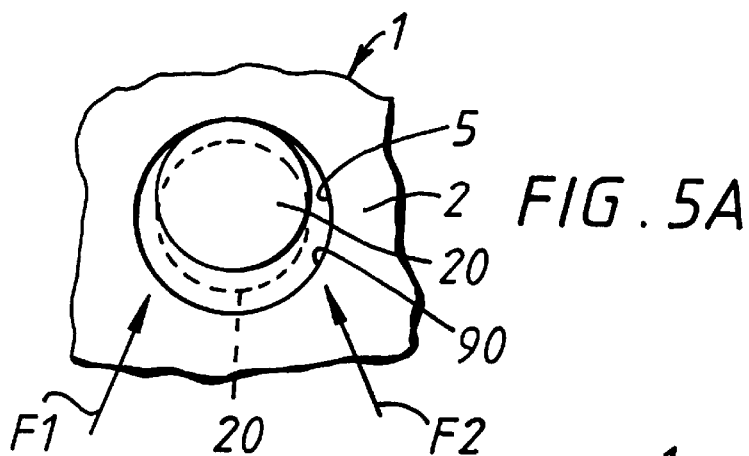
Figure 5B:
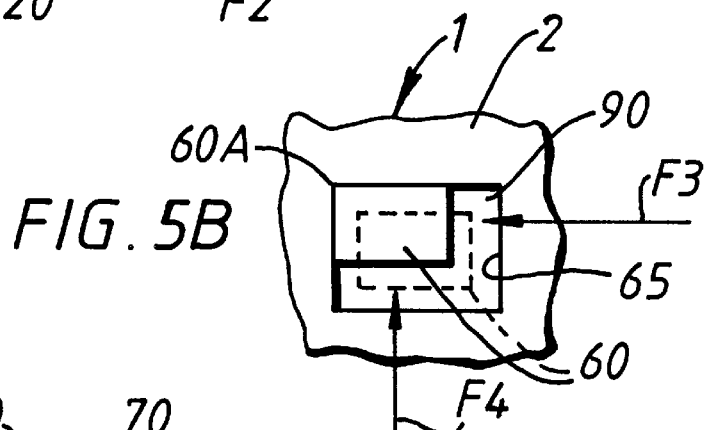
Figure 5C:
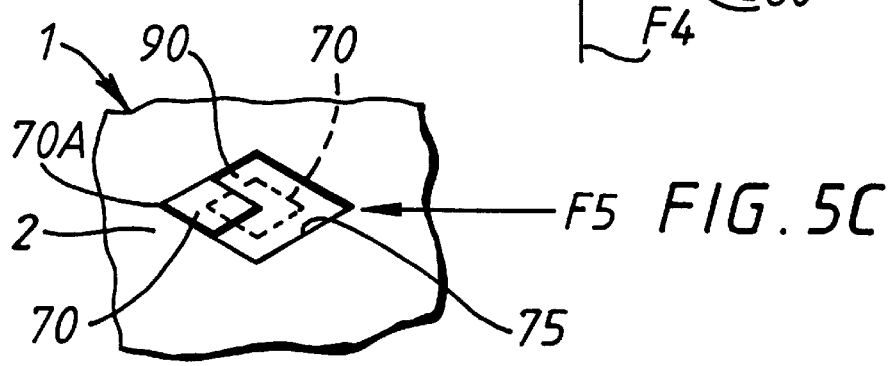
Figure 6:
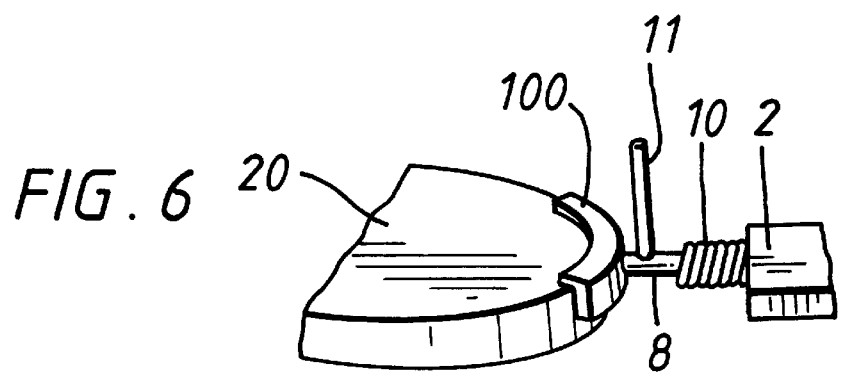

FIGS. 5A, 5B and 5C respectively illustrate plan views of differently shaped tablets in complementary shaped recesses of tablet holders and the application of clamping forces to the tablets, and FIG. 6 illustrates a clamping member profiled to co-operate in complementary manner with a tablet.

Figure 7:
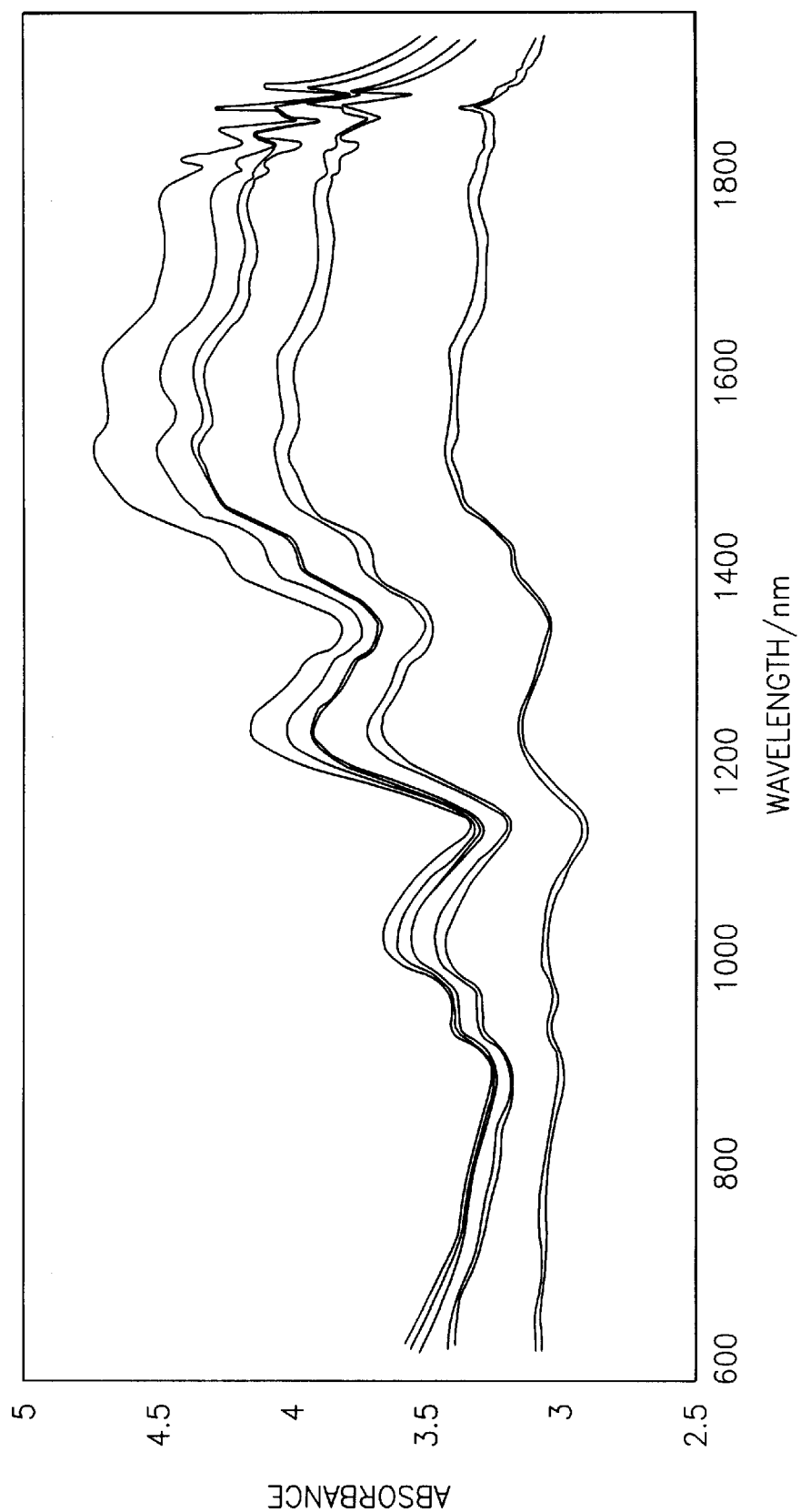

FIG. 7 illustrates the spectra acquired from a pharmaceutical tablet using a Foss Electirc INTACT analyser. Ten scans of a tablet were carried out, after removing and replacing the tablet in the same orientation.

Figure 8:
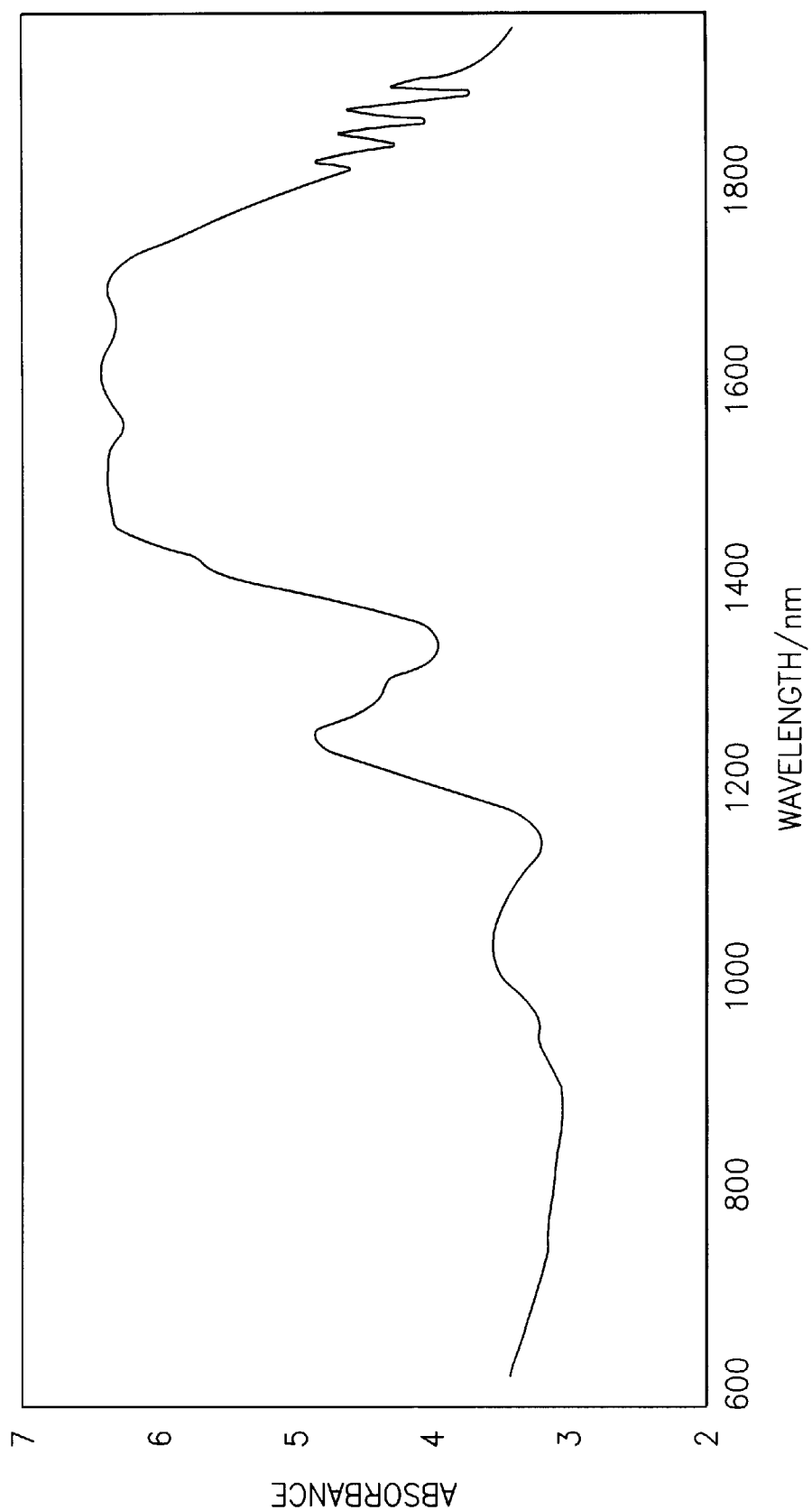

FIG. 8 shows the results from the same test used in FIG. 7 carried out using a spectrophotometric analyser according to the present invention.

DETAILED DESCRIPTION OF DRAWINGS

Figure 1:
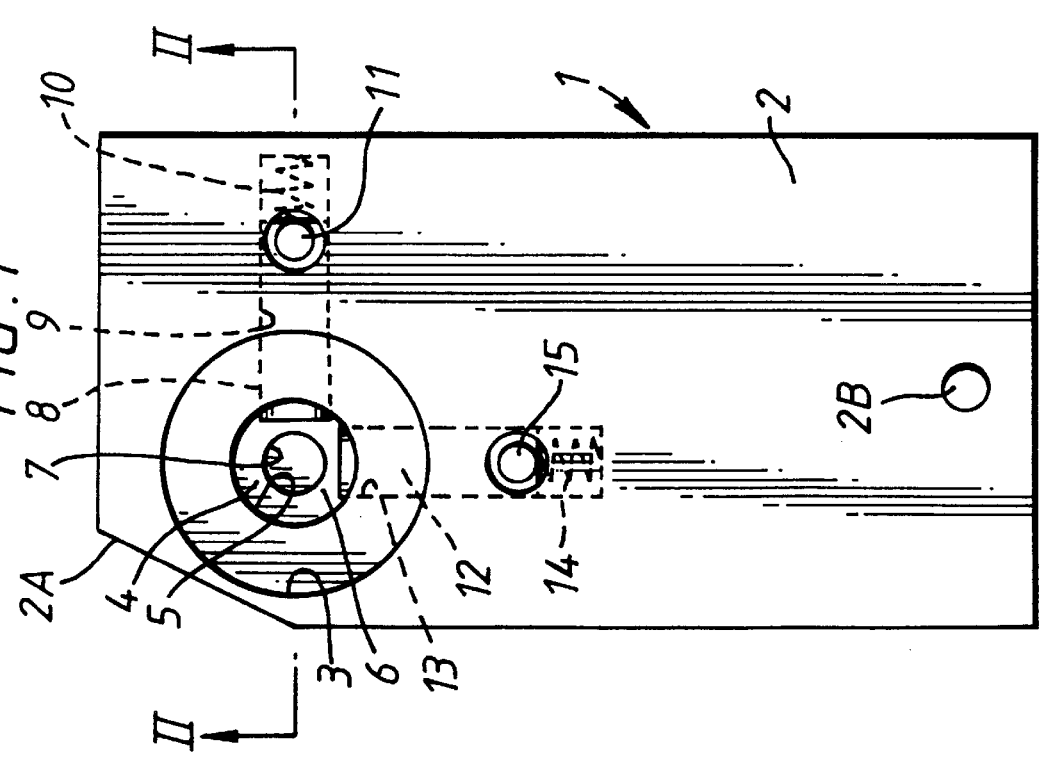

The tablet holder 1 shown in FIG. 1 is predominantly formed from a rectangular piece of aluminium plate which provides a body 2 in a side face of which is machined a cylindrical socket 3. Located in a bottom face 4 of the socket 3 is a cylindrical recess 5 that is concentric with the cylindrical socket 3. Located in a flat bottom face 6 of the recess 5 is an aperture 7 that is concentric with the socket 3 and opens through to the opposite face of the body 2.

Located in the plane of the body 1 and projecting radially into the recess 5 is a rod 8 which is slidable longitudinally in a track 9 in the body to be displaceable radially inwardly and outwardly of the recess 5 (see FIG. 2). The rod 8 is biased by a spring 10 relative to the body 2 to be urged into the recess 5. A lever 11 projects from the rod 8 and is presented for manually displacing the rod 8 against its spring loading to withdraw the rod from the recess 5. Also located in the plane of the body 2 and projecting into the recess 5 is a second rod 12 which is slidable longitudinally in a track 13 in the body to be displaceable inwardly and outwardly of the recess 5 in a direction substantially perpendicular to the direction of displacement of the rod 8. The rod 12 is biased by a spring 14 relative to the body 2 to be urged into the recess 5 similarly to the biasing of the rod 8. Also the rod 12 is provided with a lever 15 which facilitates its manual displacement against the spring biasing out of the recess 5. The holder 1 is intended to accommodate a tablet 20 (FIG. 2) which is of circular profile with opposed part spherical convex faces 21. The circular recess 5 is machined so that its diameter is slightly greater than the diameter of the tablet 20 so that with the rods 8 and 12 withdrawn against their biasing springs 10 and 14 clear of the recess 5, the tablet 20 can be located in the recess 5 (as shown in FIG. 2) with slight clearance between the circular periphery of the tablet and the cylindrical wall of the recess 5. With the tablet 20 accommodated in the recess 5, the rods 8 and 12 are released and biased by the springs 10 and 14 to act as clamps on the periphery of the tablet 20 which cause the tablet to be displaced and secured against the cylindrical wall of the recess 5. The clamping forces provided by the spring loaded rods 8 and 14 consequently displace the tablet 20 to a very small amount but sufficient to take up part of the clearance that may initially have been provided between the tablet and the cylindrical wall of the recess 5 to ensure that the tablet is displaced and secured at a predetermined position relative to and overlying the aperture 7. This position in which the tablet 20 is secured will be the same for all identical tablets 20 as may be selected for analysis from a batch of tablets as manufactured. It will be seen from FIG. 2 that in its clamped condition a part spherical face 21 of the tablet 20 is substantially concentric with the circular aperture 7 and sits in the aperture 7 to abut the periphery of that aperture and provide a reasonable closure to the passage of stray near infrared radiation to enter the aperture 21 by passing between the surface of the tablet and the periphery of the aperture 7.

The tablet holder 1 accommodating the clamped tablet 20 is now fitted to a spectrophotometer to analyse characteristics of the tablet (or of the material of the tablet) by measurements from a beam of near infrared radiation transmitted through the tablet. Conveniently the spectophotometer will be considered as that sold under the Trade Mark INTACT for a tablet analyser of Foss Electric. The tablet analyser has a substantially flat bed 30 on which the body 2 of the tablet holder 1 is slidably received in face-to-face contact and displaced to a predetermined position in which the aperture 7 overlies a port 31 of the analyser. Sited within the port 3 is a detector 32 from which spectra measurement signals are derived in known manner. To ensure that the tablet holder is accurately located at its predetermined position over the detector 32, the body 2 is slidably displaceable between an upstanding wall 33 on the bed 30 and a plate or similar component 34. The plate 34 is spring loaded at 35 relative to the flat bed 30 to bias the holder 1 against the wall 33 until that holder abuts a stop (not shown) at its predetermined position on the bed 30. It will be noted that the body 2 is provided with a chamfer 2A which serves as a convenient lead-in face to facilitate initial location of the tablet holder between the wall 33 and the spring loaded plate 34 and with a knob 2B for convenience of manoeuvring the holder on the bed 30. When at its predetermined position on the flat bed 30, the cylindrical socket 3 of the tablet holder is concentric with a cylindrical probe 40 of the tablet analyser. The probe 40 is longitudinally displaceable in the direction of its axis for its tip 41 to enter the socket 3 within which it is received as a close sliding fit. The probe 40 houses a fibre bundle 42 through which near infrared (NIR) radiation is transmitted from the source thereof to direct a beam 45 longitudinally/axially through a circular port 43 in the probe tip. The port 43 is concentric with the aperture 7 and has an area less than 90% of the area of the tablet face 21. The NIR beam 45 is directed through the port 43 to the tablet 20 whilst an NIR beam 46 consequently transmitted through the tablet 20 is applied to the detector 32 to provide measurements from which characteristics of the tablet material or structure are analysed. It will be seen from FIG. 2 that the NIR beam 45 is directed to the face of the tablet 20 in a direction which is substantially perpendicular to the plane in which the clamping force components provided by the spring loaded rods 8 and 12 are applied to the periphery of the tablet 20.

The probe 40 is displaceable longitudinally of its axis to enter the socket 3 and during such displacement the tip 41 preferably abuts the tablet 20 to apply pressure to the tablet and urge it onto the bottom face 6 of the recess 5. This may further secure the tablet in its predetermined position in the holder 1 and also improve the light seal effected by abutment of the tablet with the bottom face 6 of the recess 5. The probe 40 usually will be spring loaded to alleviate undue pressure being applied to the tablet 20 to ensure that the integrity of the tablet is maintained. The probe 40 can be withdrawn from the tablet holder and the tablet holder withdrawn from the tablet analyser so that the tablet 20 can be replaced by a further sample tablet selected from a batch of tablets; characteristics of the tablets or their material/pharmaceutical structure can thus be analysed to determine the acceptability of the batch of tablets for marketing purposes as previously discussed. Because each tablet 20 is securely clamped in a predetermined position in the tablet holder 1 and the tablet holder 1 is securely clamped at a predetermined position in the tablet analyser on the bed 30 relative to the detector 32, it may be ensured that all similarly shaped and sized tablets of a particular batch will be presented for spectrophotometric analysis under the same conditions. In the event that one or more of the tablet faces 21 carries embossing or score lines it will be appreciated that the tablets selected from a particular batch must be located in the tablet holder in the same orientation.

As an indication of the efficiency with which analysis measurements may be reproduced by use of the method and apparatus as above described with reference to FIGS. 1 and 2, the analysis measurements for the coinciding graphs shown in FIG. B of the accompanying illustrative drawings resulted from use of that method and apparatus whilst the array of graphs shown in FIG. A of the accompanying illustrative drawings resulted from the same tablet being subjected to spectrophotometric analysis by a method and apparatus similar to that shown in FIGS. 1 and 2 but with the spring loaded clamping rods 8 and 12 omitted (so that the tablet 20 could be located in the recess 5 at an infinite number of variable positions as permitted by the relatively small clearance provided between the periphery of the tablet and the wall of the recess 5). The measurements derived from the graphs of FIG. A are not sufficiently accurate to be relied on for assessing the acceptability of the structure or composition of a pharmaceutical tablet; however measurements from the graph of FIG. B and certainly acceptable for manufacturing purposes. The method and apparatus of FIGS. 1 and 2 may be used to advantage therefor to provide a rapid non-destructive quality assessment of tablets during production so reducing the manufacturing cycle time with considerable cost savings.

Figure 3:
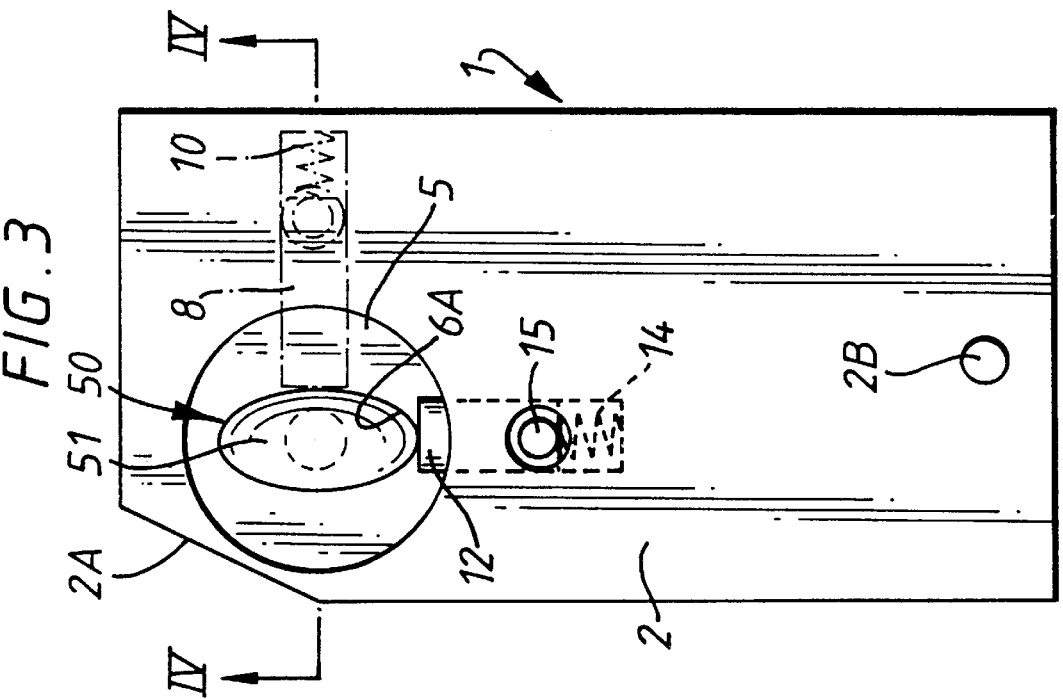
FIG. 3 is a modified form of tablet holder suitable for a different shape of tablet from that shown in FIG. 1.

The recess 5 of the tablet holder will usually be machined or otherwise formed in the body 2 for accommodating a particular and predetermined tablet so that several tablet holders may be available, each with a different shape and size of recess 5 depending upon the respective tablets which are to be subjected to spectrophotometric analysis. The bottom face 6 of the recess 5 may be profiled to correspond with the face 21 of the tablet so that when the tablet is accommodated in the recess 5 the face 21 of the tablet abuts the bottom face 6 in substantially complementary fashion. This has been found to improve the light sealing characteristics between the tablet and the recess 5 and also to assist in the retention of the tablet at the predetermined position when subjected to the clamping force. With this in mind FIGS. 3 and 4 show a modified form of tablet holder for an oval tablet 50 having opposed part cylindrical faces 51 where the recess 5 is elongated to correspond to the profile of the oval tablet and has its bottom face 6A of part cylindrical concave profile to correspond to the profile of the surface 51. Consequently when the tablet 50 is accommodated in the recess 5 a face 51 of the tablet abuts the surface 6A in substantially complementary manner to alleviate movement between the tablet and the holder and also to alleviate light leakage to the aperture 7 between the tablet and the surface 6A. The modified holder 1 shown in FIGS. 3 and 4 is provided with a spring loaded clamping rod 12 similar to that of the embodiment in FIG. 1 so that a clamping force is applied to the tablet 50 to displace that tablet to a predetermined position at the end of its seating 6A remote from the clamp 12. Because of the elongated structure of the tablet 50 and the close co-operation between the surface of the tablet and the surface 6A, a single clamp 12 may be adequate to secure the tablet at the predetermined position relative to the body 2. If required however the second spring loaded clamping rod 8 may be provided (as indicated by broken lines in FIG. 3) in a similar manner to the arrangement of FIG. 1.

FIGS. 5A, 5B and 5C illustrate examples by which differently shaped tablets (respectively a circular tablet 20, a rectangular tablet 60 and a lozenge shaped tablet 70) may be subjected to clamping forces in the tablet holders 1 to be displaced to respective predetermined positions in their respective complementary shaped recesses 5, 65 and 75. In these Figures each tablet may initially be located in its respective recess 5, 65 and 75 at the positions of tablets 20, 60 and 70 shown in ghost/dotted outline. For convenience of description, a clearance 90 provided between the periphery of each tablet and the periphery of the complementary shaped recess 5, 65 and 75 in which the respective tablet is received is shown greatly exaggerated. In practice the clearance 90 will be as small as conveniently possible to permit location of the tablet in the recess and removal of the tablet from the recess. The initial location of each tablet in its recess is capable of an infinitely variable number of possibilities within whatever clearance 90 is available. However by subjecting each tablet to the clamping force in the plane of the plate body 2, the tablet can be displaced relative to the recess in which it is received so that it closes part of the clearance 90 and firmly abuts the peripheral wall of the recess at a predetermined position in which it is temporarily maintained by the clamping force. In FIG. 5A the circular tablet 20 is subjected to two clamping forces F1, F2, directed at 45° relative to each other and generally radially of the recess 20 to displace the tablet 20 to and maintain it at its predetermined position. In FIG. 5B the rectangular tablet 60 is subjected to two clamping forces F3, F4 directed at 90° relative to each other and generally parallel to respective side walls of the recess 65 so that in its predetermined position an external corner 60A of the tablet 60 mates with an internal corner of the recess 65 with mutually perpendicular side faces of the tablet abutting side faces of the recess 65. The lozenge tablet 70 in FIG. 5C is subjected to a single clamping force F5 which is directed through co-inciding apices of the recess and the tablet so that the tablet is displaced for an external apex 70A thereof to mate with an internal apex of the recess 75 with side faces of the tablet (which extend from the apex 70A) abutting side faces of the recess 75.

FIG. 6 shows a clamping member comprising the spring loaded rod 8 including a clamping plate 100 carried on the rod 8. The plate 100 is intended to abut the tablet 20 (to effect its displacement to the predetermined position) and is profiled in size and shape to engage in complementary relationship with the part of the tablet which it abuts.

We claim:

1. A method of spectrophotometrically analysing characteristics of a tablet by transmission measurements from a beam of electromagnetic radiation applied to and passing through the tablet which comprises locating the tablet in a recess to overlie an aperture through which aperture radiation from the beam transmitted through the tablet is applied to a detector for analysis measurements, characterised by applying to the tablet a clamping force in a direction substantially perpendicular relative to the direction in which the beam is applied to the tablet and which clamping force serves to secure the tablet at a predetermined position within and relative to the recess.

2. A method as claimed in claim 1 which comprises securing the recess at a predetermined position relative to the detector.

3. A method as claimed in claim 2 which comprises applying to the tablet a clamping force derived from two clamping force components that are directed to the tablet substantially perpendicularly relative to each other.

4. A method as claimed in claim 3 in which the two clamping force components are located in a common plane which plane is substantially perpendicular relative to the direction which the beam is applied to the tablet.

5. A method as claimed in claim 4 which comprises forming the recess with a peripheral shape that is substantially complementary to the peripheral shape of the tablet for the tablet to be closely received in the recess.

6. A method as claimed in claim 5 which comprises forming the recess with a bottom face which presents a substantially complementary profile to a face of the tablet which is to be received in the recess for that face of the tablet to co-operate with the bottom face of the recess in substantially complementary fashion.

7. A method as claimed in claim 6 which comprises applying pressure to the tablet in a direction corresponding to that in which the beam is applied to the tablet to urge the tablet against the or a bottom face of the recess.

8. A spectrophotometric apparatus for analysis of characteristics of a tablet by transmission measurements from a beam of electromagnetic radiation applied to and passing through the tablet which comprises a recess for accommodating a tablet during the analysis, said recess having a bottom face in which is located an aperture through which radiation transmitted through the tablet is directed, and a detector responsive to said transmitted radiation for analysing characteristics of the tablet, and in which clamping means is provided for securing a tablet in the recess by applying a clamping force to the tablet in a direction substantially perpendicular relative to the direction in which the beam is applied to the tablet to displace the tablet relative to the recess to a predetermined position in the recess and to secure the tablet at said predetermined position in the recess.

9. Apparatus as claimed in claim 8 and comprising securing means for securing the aperture at a predetermined position relative to the detector.

10. Apparatus as claimed in claim 9 in which the clamping means comprises at least one spring loaded clamping member located at the periphery of the recess for abutting the periphery of a tablet accommodated in the recess.

11. Apparatus as claimed in claim 10 and comprising two said spring loaded clamping members disposed to direct two clamping force components on a tablet accommodated in the recess which clamping force components are directed substantially perpendicularly relative to each other.

12. Apparatus as claimed in claim 11 in which the two clamping force components are in a plane which is substantially perpendicular relative to the direction in which the beam is applied to the tablet.

13. Apparatus as claimed in claim 12 in which the bottom face of the recess is substantially flat.

14. Apparatus as claimed in claim 12 in which the bottom face of the recess is profiled to present a substantially concave surface within which a tablet is to be seated.

15. Apparatus as claimed in claim 14 in which the beam is directed longitudinally and is derived from a probe which probe is longitudinally displaceable relative to the recess to be capable of abutting a tablet in the recess and applying pressure to the tablet to urge it against the bottom face of the recess.

16. Apparatus as claimed in claim 15 in which the recess, aperture and clamping means are provided in a tablet holder, which holder is removable from the apparatus for convenience of locating a tablet in and removing a tablet from the recess.

17. Apparatus as claimed in claim 16 and comprising means for securing the tablet holder with its aperture at a predetermined position relative to the detector.

18. Apparatus as claimed in claim 17 in which the securing means for the tablet holder comprises a spring loaded member by which the tablet holder is securely clamped at the predetermined position on a bed within which the detector is located.

19. Apparatus as claimed in claim 18 in which the clamping means is profiled for co-operating with a tablet in the recess in substantially complementary manner with the part of the tablet with which it engages.

20. Apparatus as claimed in claim 13 in which the beam is directed longitudinally and is derived from a probe which probe is longitudinally displaceable relative to the recess to be capable of abutting a tablet in the recess and applying pressure to the tablet to urge it against the bottom face of the recess.

21. Apparatus as claimed in claim 20 in which the recess, aperture and clamping means are provided in a tablet holder, which holder is removable from the apparatus for convenience of locating a tablet in and removing a tablet from the recess.

22. Apparatus as claimed in claim 21 and comprising means for securing the tablet holder with its aperture at a predetermined position relative to the detector.

23. Apparatus as claimed in claim 22 in which the securing means for the tablet holder comprises a spring loaded member by which the tablet holder is securely clamped at the predetermined position on a bed within which the detector is located.

24. Apparatus as claimed in claim 23 in which the clamping means is profiled for co-operating with a tablet in the recess in substantially complementary manner with the part of the tablet with which it engages.

25. A spectrophotometric analysis tablet holder comprising a body, a recess in the body for accommodating a tablet, said recess having a bottom face in which is located an aperture through which radiation transmitted through the tablet is to be applied to a detector for analysing characteristics of the tablet and in which clamping means is carried by the body for securing a tablet in the recess by applying a clamping force to the tablet to displace the tablet relative to the recess to a predetermined position in the recess and to secure the tablet at said predetermined position in the recess.

26. A holder as claimed in claim 25 in which the clamping means comprises at least one clamping component which is spring loaded relative to the body for engaging the periphery of a tablet in the recess to apply the clamping force.

27. A holder as claimed in claim 26 in which two said clamping components are provided which are spring loaded relative to the body, said components applying clamping force components to the periphery of the tablet which components are directed substantially perpendicularly relative to each other.

28. A holder as claimed in claim 27 in which the body comprises a substantially flat plate with the recess opening into a side face thereof and the clamping means applies a clamping force to the tablet substantially in the plane of the plate body.

29. A holder as claimed in claim 28 in which the clamping means is profiled for co-operating with a tablet in the recess in substantially complementary manner with the part of the tablet with which it engages.

* * * * *